(12) United States Patent
Park

(10) Patent No.: US 10,006,869 B1
(45) Date of Patent: Jun. 26, 2018

(54) APPARATUS FOR INSPECTING SURFACE OF CYLINDRICAL BODY

(75) Inventor: Won Jae Park, Gyeonggi-do (KR)

(73) Assignee: P&S TECHNOLOGY CO., LTD., Gyeonggi-do (KR)

( * ) Notice: Subject to any disclaimer, the term of this patent is extended or adjusted under 35 U.S.C. 154(b) by 1327 days.

(21) Appl. No.: 13/590,576

(22) Filed: Aug. 21, 2012

(30) Foreign Application Priority Data

Aug. 26, 2011 (KR) .......................... 10-2011-0085510

(51) Int. Cl.
*G01N 21/88* (2006.01)
*G02B 26/10* (2006.01)

(52) U.S. Cl.
CPC ....... *G01N 21/8851* (2013.01); *G02B 26/105* (2013.01)

(58) Field of Classification Search
CPC ............................ G01N 21/952; G01N 21/956
USPC .............................. 356/239.4–239.6; 382/142
See application file for complete search history.

(56) References Cited

U.S. PATENT DOCUMENTS

| | | | | |
|---|---|---|---|---|
| 4,221,961 A | * | 9/1980 | Peyton | G01N 21/9018 250/223 B |
| 4,385,233 A | * | 5/1983 | Lovalenti | B07C 5/126 209/526 |
| 4,584,469 A | * | 4/1986 | Lovalenti | G01N 21/90 250/223 B |
| 4,866,263 A | * | 9/1989 | Fukuchi | G01N 21/9045 250/223 B |
| 5,267,033 A | * | 11/1993 | Hoshino | H04N 7/181 250/223 B |
| 5,404,227 A | * | 4/1995 | Sumita | B07C 5/126 198/343.1 |
| 2005/0117149 A1 | * | 6/2005 | Grindinger | B07C 5/3408 356/239.4 |
| 2010/0177381 A1 | * | 7/2010 | Lippert | G02B 21/26 359/398 |

FOREIGN PATENT DOCUMENTS

| | | |
|---|---|---|
| KR | 10-0751266 | 8/2007 |
| KR | 10-2008-0041325 | 5/2008 |
| KR | 10-0831368 | 5/2008 |

OTHER PUBLICATIONS

Berardinis, Larry. "Motion Design 101: Gears and belts", http://www.machinedesign.com/technologies/motion-design-101-gears-and-belts. Mar. 1, 2000.*

* cited by examiner

*Primary Examiner* — Rebecca C Bryant
(74) *Attorney, Agent, or Firm* — Bacon & Thomas, PLLC

(57) ABSTRACT

An apparatus for inspecting a surface of a cylindrical body includes an arranging unit configured to arrange a plurality of cylindrical bodies at regular intervals; and a circular conveyor configured to rotate while keeping in contact with the arranging unit, receive the arranged cylindrical bodies in order and move the received cylindrical bodies in a circumferential direction. Further, the apparatus includes a plurality of clamp units configured to be arranged around a circumstance of the circular conveyor at predetermined intervals, receive the cylindrical bodies in order; and a photographing unit configured to photograph surfaces of the clamped cylindrical bodies in order. Furthermore, the apparatus includes a control unit configured to analyze the surface of each of the cylindrical bodies and determine whether the surface is defective or not.

16 Claims, 11 Drawing Sheets

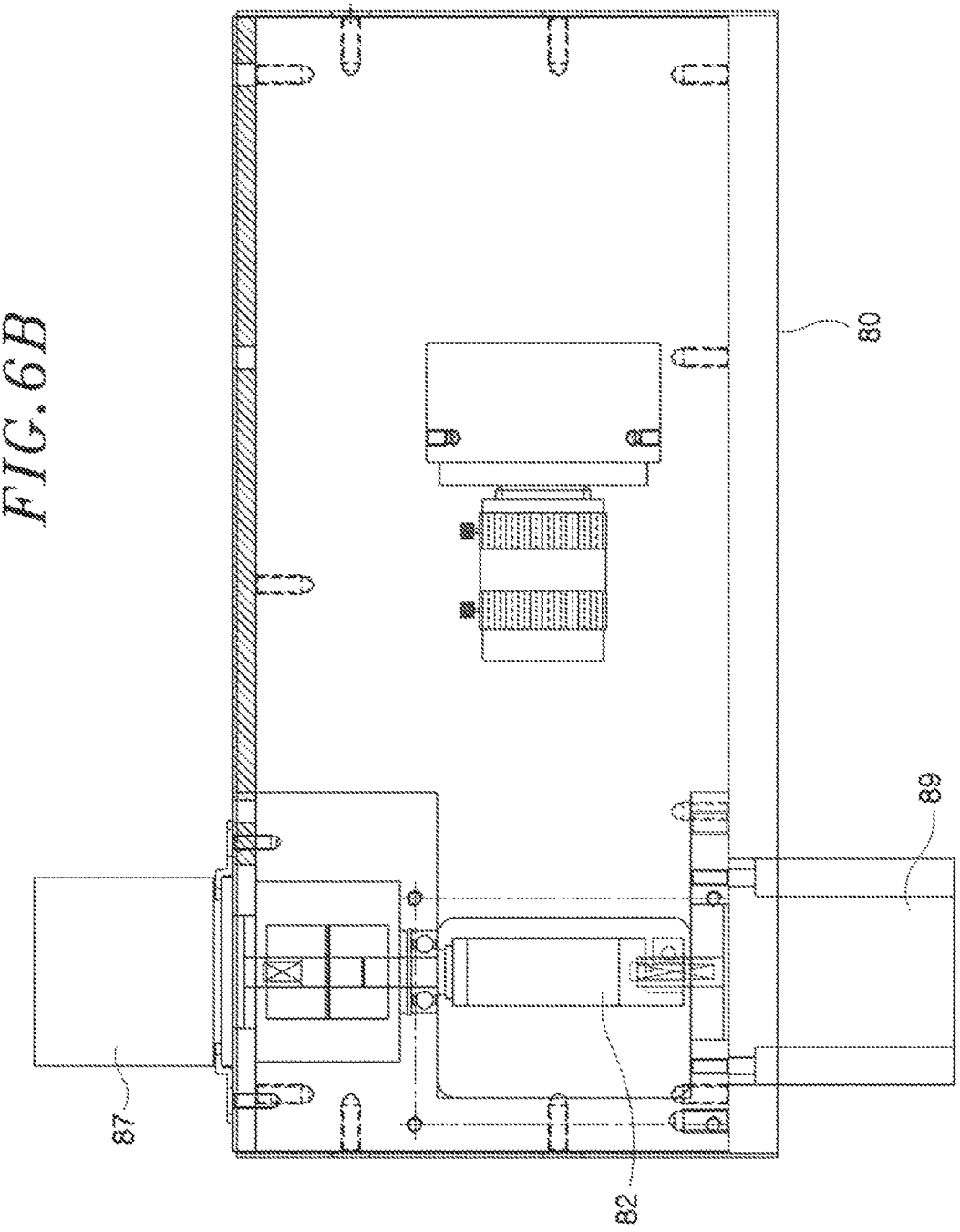

APPARATUS FOR INSPECTING SURFACE OF CYLINDRICAL BODY

CROSS-REFERENCE TO RELATED APPLICATION(S)

The present invention claims priority of Korean Patent Application No. 10-2011-0085510, filed on Aug. 26, 2011, which is incorporated herein by reference.

FIELD OF THE INVENTION

The present invention relates to an apparatus for inspecting a surface of a cylindrical body.

BACKGROUND OF THE INVENTION

Producing nuclear fuel includes converting and enriching uranium ore concentrate, and then making it into a ceramic form, having the size of a little fingernail, which is called a sintered uranium dioxide pellet ($UO_2$ pellet). Subsequently, several hundreds of the $UO_2$ pellets are put in a metal tube, and the metal tube is sealed, thus forming a fuel rod. Several hundreds of the fuel rods are thereafter fastened to a strong metal structure, forming a bundle of nuclear fuel rods. Typically, about one hundred fifty bundles of nuclear fuel rods are placed in a nuclear reactor of a nuclear power plant and take part in a fission chain reaction, thus generating heat.

Making nuclear fuel for light-water reactors includes converting low enriched uranium hexafluoride ($UF_6$) into uranium dioxide ($UO_2$) powder. Methods of this conversion are classified into a wet process in which water makes contact with uranium, and a dry process in which vapor makes contact with uranium. Preferably, a dry conversion process may be used, because there is a financial advantage in that equipment is simple, so the manufacturing costs are low.

$UO_2$ powder that has been produced by the dry conversion process is homogenized, and formed into a cylindrical powder compact, the length of which is 10 mm, after a powder preparation process. The powder compact is thereafter sintered at high temperatures ranging 1700° C. to 1750° C. and then ground to form a sintered pellet having a predetermined diameter. The sintered pellet is finally completed through cleaning and drying processes. The completed sintered $UO_2$ pellet has a weight of about 5.2 g and a diameter of about 8.05 mm. Approximately 356 sintered $UO_2$ pellets may be charged into each fuel rod, and 96,000 may be charged into each bundle of fuel rods.

FIG. 1 is a perspective view showing the external appearance of a cylindrical sintered $UO_2$ pellet. A sintered $UO_2$ pellet p is manufactured into a ceramic form that is hard and safe. The sintered $UO_2$ pellet p has a cylindrical shape, which has a side surface s, an upper surface and a lower surface f and has a predetermined diameter.

If the sintered $UO_2$ pellet p, especially, the side surface s thereof, is defective, it may not be used as nuclear fuel. Therefore, inspection whether the surface of the $UO_2$ pellet p is defective or not is required. Hereinafter, the term 'surface' refers to the side surface s'.

As described above, a large amount of sintered $UO_2$ pellets are necessary in a nuclear plant. Thus, an apparatus that can rapidly and precisely inspect the surfaces of a lot of $UO_2$ pellets is required.

SUMMARY OF THE INVENTION

In view of the above, the present invention provides an apparatus which is capable of rapidly and precisely inspecting the surface of a cylindrical body, such as a sintered $UO_2$ pellet and the like.

In accordance with an embodiment of the present invention, there is provided an apparatus for inspecting a surface of a cylindrical body. The apparatus for inspecting the surface of the cylindrical body includes an arranging unit configured to arrange a plurality of cylindrical bodies at regular intervals; a circular conveyor configured to rotate while keeping in contact with the arranging unit, receive the arranged cylindrical bodies in order and move the received cylindrical bodies in a circumferential direction; a plurality of clamp units configured to be arranged around a circumstance of the circular conveyor at predetermined intervals, receive the cylindrical bodies in order, each of the clamp units configured to clamp both ends of the corresponding cylindrical body and rotate the clamped cylindrical body; a photographing unit configured to photograph surfaces of the clamped cylindrical bodies in order; a control unit configured to analyze the surface of each of the cylindrical bodies and determine whether the surface is defective or not, wherein each of the cylindrical bodies makes one rotation by the corresponding clamp unit while it is moved by the circular conveyor in the circumferential direction thereof by a specific distance, and while the cylindrical body makes one rotation, the photographing unit traces the cylindrical body to photograph same, thereby to photograph an entire side surface of the cylindrical body that corresponds to 360°.

In accordance with the present invention, it is possible to rapidly and precisely inspect whether the surfaces, especially, the side surfaces, of cylindrical bodies, such as sintered $UO_2$ pellets, and the like, are defective or not.

Further, transferring, inspecting and picking out the cylindrical bodies are automatically conducted in a single system. Therefore, labor consumption can be minimized, and the efficiency of utilization of space can be improved.

Further, a camera uses a reflector and thus is able to trace a cylindrical body without moving thereof and takes an image of the surface of the cylindrical body. Furthermore, the present invention has a mechanism in which a clamp unit rotates the cylindrical body by a precise angle. Therefore, it is possible to precisely and efficiently inspect the entire area of the side surface of the cylindrical body that corresponds to 360°.

BRIEF DESCRIPTION OF THE DRAWINGS

The objects and features of the present invention will become apparent from the following description of preferred embodiments given in conjunction with the accompanying drawings, in which:

FIGS. 6A and 6B are front views of a photographing unit shown in FIG. 2A in a mechanical cam type and an electric motor (servo) type, respectively;

DETAILED DESCRIPTION OF THE EMBODIMENTS

Figure 1:
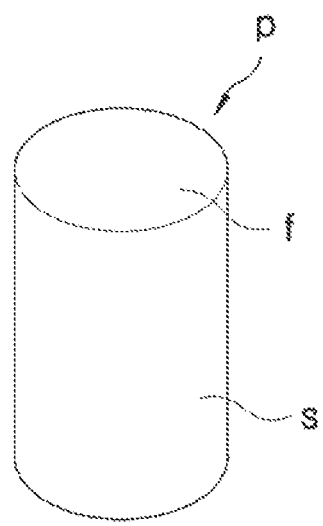
FIG. 1 is a perspective view showing a cylindrical sintered $UO_2$ pellet.

In the following description of the present invention, if the detailed description of the already known structure and operation may confuse the subject matter of the present invention, the detailed description thereof will be omitted.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Hereinafter, an embodiment of the present invention will be described in detail with reference to the accompanying drawings so that they can be readily implemented by those skilled in the art. Reference now should be made to the drawings, throughout which the same reference numerals are used to designate the same or similar components, and overlapping descriptions will be omitted.

An embodiment of the present invention provides an apparatus for rapidly and precisely inspecting the surface of a cylindrical body. The cylindrical body may be a sintered pellet that is produced by sintering. The cylindrical body may be a sintered uranium dioxide pellet that is used as nuclear fuel in a light-water reactor.

Referring to FIG. 1, a sintered uranium dioxide pellet or cylindrical body p is defined as being formed in a cylindrical shape that has a side surface s, an upper surface and a lower surface f and has a predetermined diameter. Hereinafter, the term 'surface' refers to the side surface s.

The construction and function of the apparatus for inspecting the surface of a cylindrical body in accordance with the embodiment of the present invention will be described.

Figure 2A:
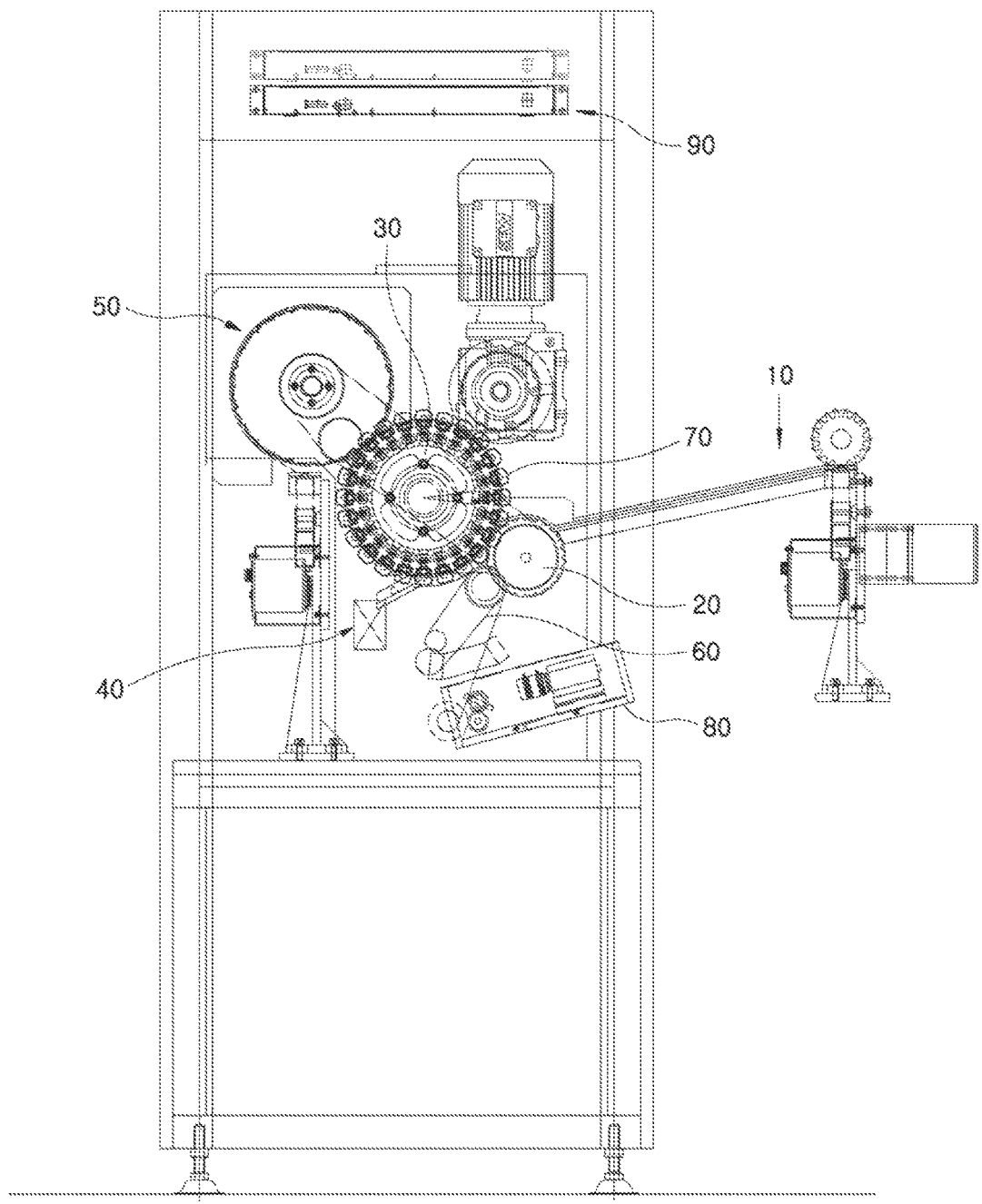
FIGS. 2A and 2B are a front view s and a plane view of an apparatus for inspecting the surface of a cylindrical body, in accordance with an embodiment of the present invention, respectively.
Figure 2B:
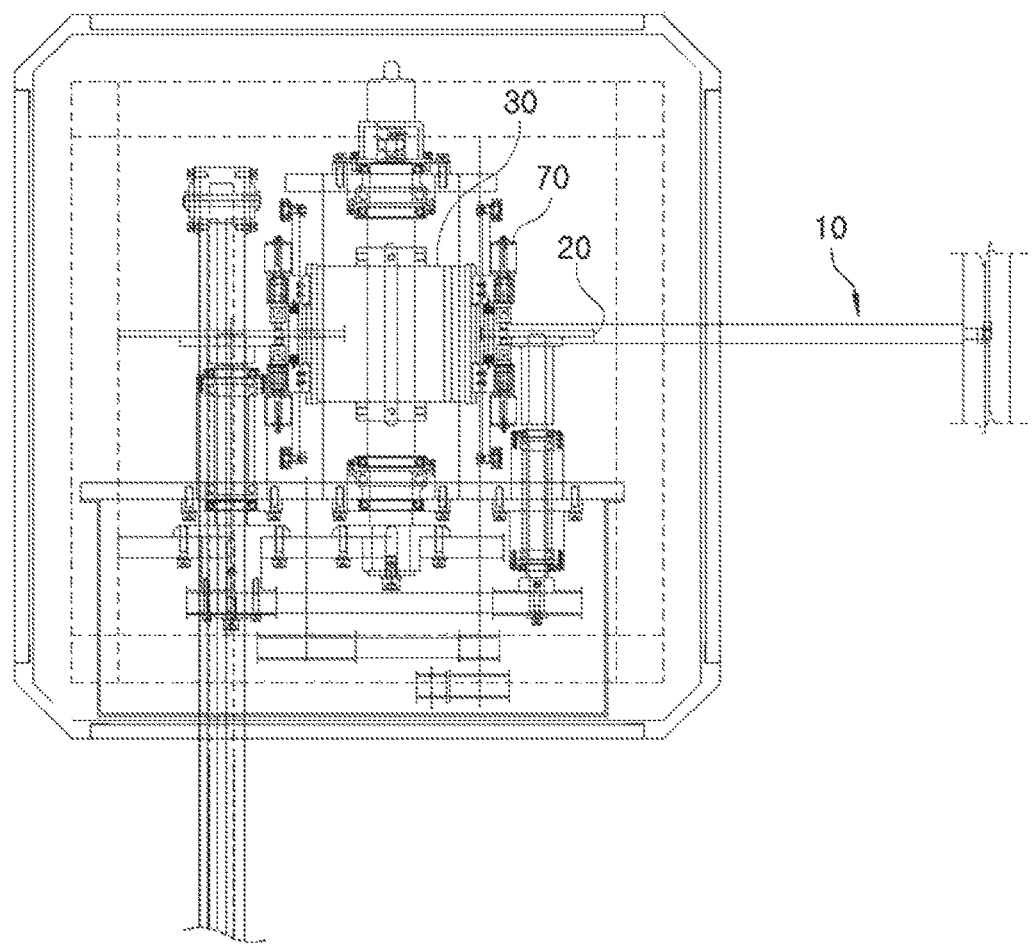

FIGS. 2A and 2B are a front view and a plane view of the apparatus for inspecting the surface of a cylindrical body in accordance with the embodiment of the present invention, respectively.

The apparatus for inspecting the surface of the cylindrical body includes an input unit 10, an arranging unit 20, a circular conveyor 30, clamp units 70, a rotary belt 60, a photographing unit 80, a control unit 90, a collecting unit 40 and a discharge unit 50.

Figure 3A:
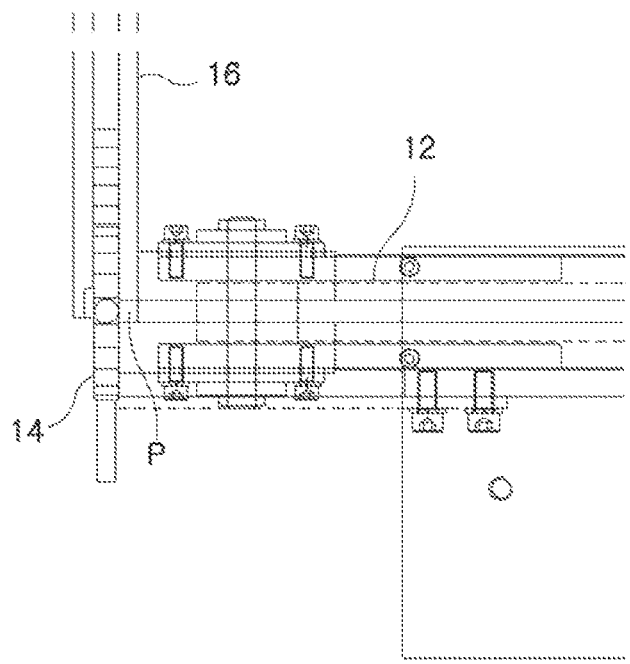
FIGS. 3A and 3B are a plane view and a front view of an input unit shown in FIGS. 2A and 2B, respectively.
Figure 3B:
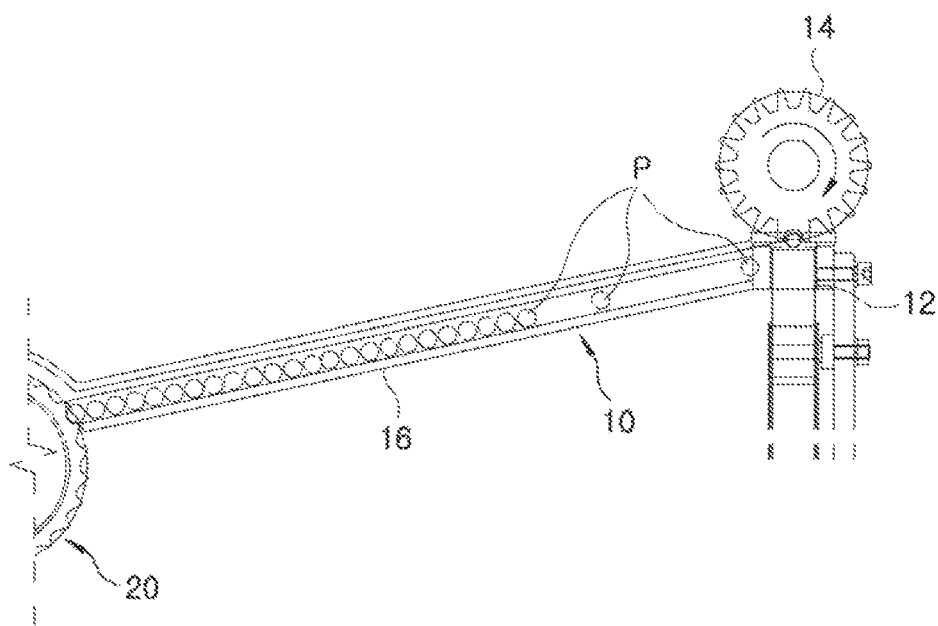

FIGS. 3A and 3B are a plane view and a front view of the input unit 10 shown in FIGS. 2A and 2B, respectively.

The input unit 10 includes an inclined rail 16, a toothed wheel 14 having a plurality of teeth, and a tray 12 in which cylindrical bodies p are loaded. The toothed wheel 14 rotates and uses the teeth to push the cylindrical bodies P from the tray 12 into the inclined rail 16. The inclined rail 16 extends a predetermined length in an inclined direction. The cylindrical bodies p are in a standby state in the inclined rail 16 and are input one after another into the arranging unit 20 by the force of gravity.

Many cylindrical bodies p may be rapidly and easily transferred into the arranging unit 20 by the input unit 10.

Figure 4:
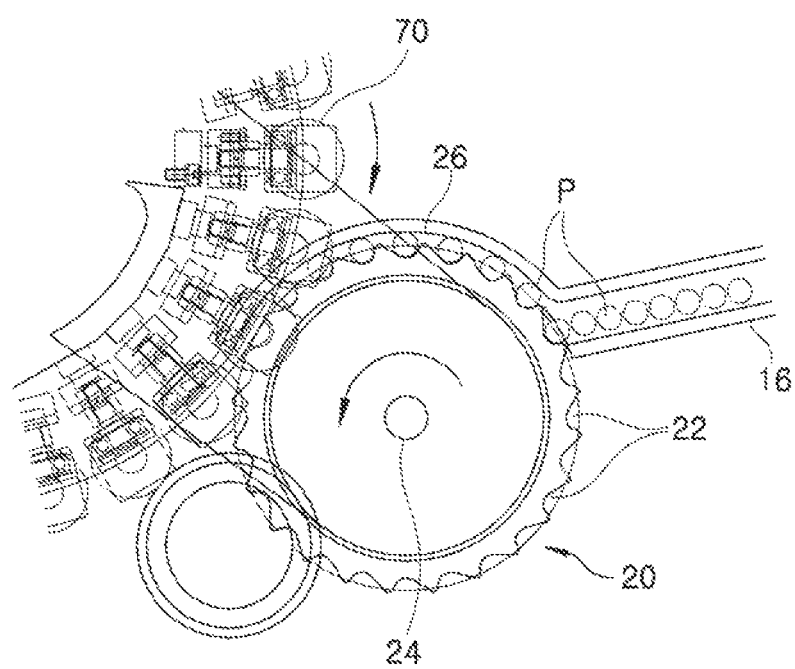
FIG. 4 is a front view of an arranging unit shown in FIGS. 2A and 2B.

FIG. 4 is a front view of the arranging unit 20 shown in FIGS. 2A and 2B.

The arranging unit 20 arranges the cylindrical bodies p at regular intervals. The arranging unit 20 has a shape of a star wheel, which rotates in a circumferential direction and has a plurality of pockets 22 arranged around the circumstance thereof at regular intervals so that the cylindrical bodies p are inserted into the corresponding pockets 22. As the arranging unit 20 rotates, the cylindrical bodies p that have been in the standby state in the inclined rail 16 are inserted into the pockets 22 one by one and move in the circumferential direction. The arranging unit 20 includes a vacuum pump 24 which adsorbs the cylindrical bodies p that have been inserted into the pockets 22. The arranging unit 20 further includes a guide which is formed outside the pockets 22 in the circumferential and functions to prevent the cylindrical bodies p inserted into the pockets 22 from being undesirably removed therefrom.

As described above, the arranging unit 20 rapidly arranges the cylindrical bodies p at precise intervals and transfers the cylindrical bodies p to the circular conveyor 30 to prepare them for inspection.

Figure 5A:
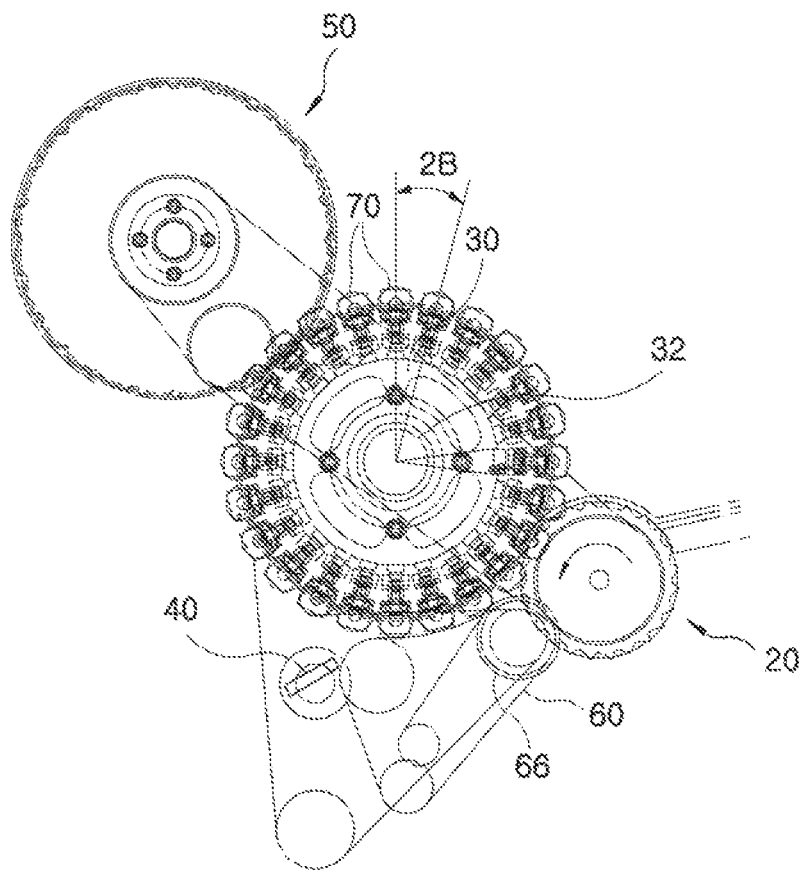
FIGS. 5A and 5B are a front view and a plane view of a circular conveyor and clamp units shown in FIGS. 2A and 2B, respectively.
Figure 5B:
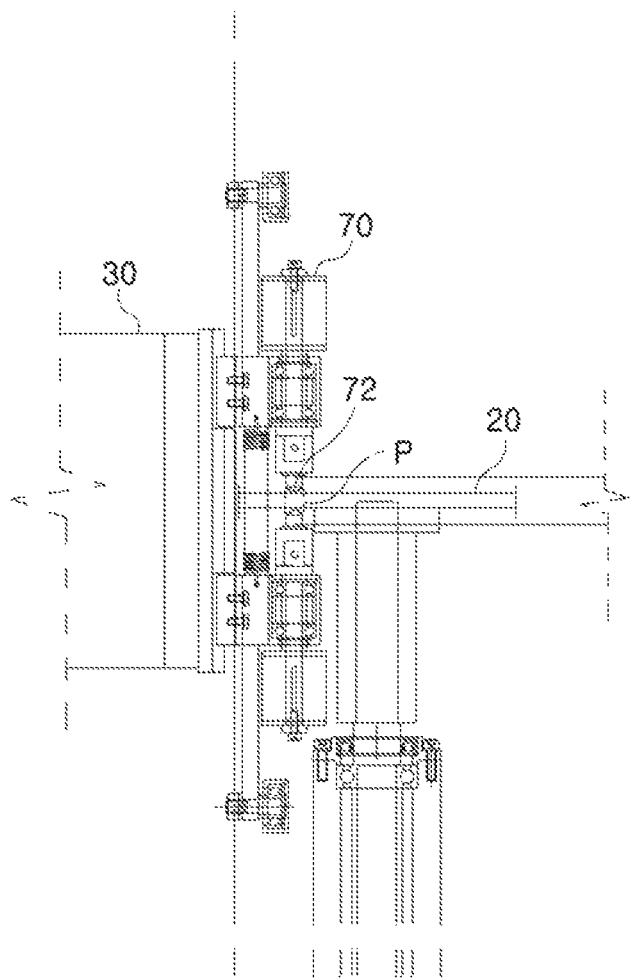

FIGS. 5A and 5B illustrate the circular conveyor 30 and the clamp units 70 shown in FIGS. 2A and 2B, respectively.

The circular conveyor 30 rotates while keeping in contact with the arranging unit 20. The circular conveyor 30 and the arranging unit 20 rotate such that they move in the same direction along the tangent therebetween. The circular conveyor 30 receives, in order, the cylindrical bodies p that haven been arranged and moves them in the circumferential direction. The rotational speeds of the circular conveyor 30 and the arranging unit 20 are controlled so that the cylindrical bodies p that haven been arranged are transmitted to the clamp units 70 at a ratio of 1:1.

The clamp units 70 are arranged around the circumstance of the circular conveyor 30 at predetermined intervals 2B. Each clamp unit 70 clamps both ends of the corresponding cylindrical body p, i.e., the upper surface and lower surface f of the cylindrical body p. Each clamp unit 70 includes two clamp tips 72 which are disposed spaced apart from each other by a predetermined distance, and each of which is made of hard or soft material. The clamp unit 70 may be implemented in the same manner as that of a ball plunger or the like. The cylindrical body p is inserted between and clamped by the two clamp tips 72 under pressure.

As the circular conveyor 30 rotates, the clamp units 70 revolve around the circular conveyor 30 while moving the cylindrical bodies P in the circumferential direction. Furthermore, each clamp unit 70 rotates on its own axis, thus rotating the clamped cylindrical body P. The rotational speed of the circular conveyor 30 or the speed at which the clamp units 70 move in the circumferential direction, and the speed at which each clamp unit 70 rotates on its own axis are controlled such that each clamp unit 70 rotates once on its own axis while it moves to half of the interval 2B between the clamp units 70.

The rotary belt 60 rotates while keeping in contact with the clamp units 70. The rotary belt 60 allows the clamp units 70 to only rotate around an area in which each of the cylindrical bodies p of is photographed. A belt drive shaft 66 that moves the rotary belt 60 is rotated in conjunction with a rotating shaft 32 of the circular conveyor 30.

The mechanism of rotating the cylindrical body p using the clamp unit 70 at a precise angle makes it possible to precisely and efficiently inspect the surface of the cylindrical body p, i.e., the entire area of the side surface s that corresponds to 360°.

Figure 6A:
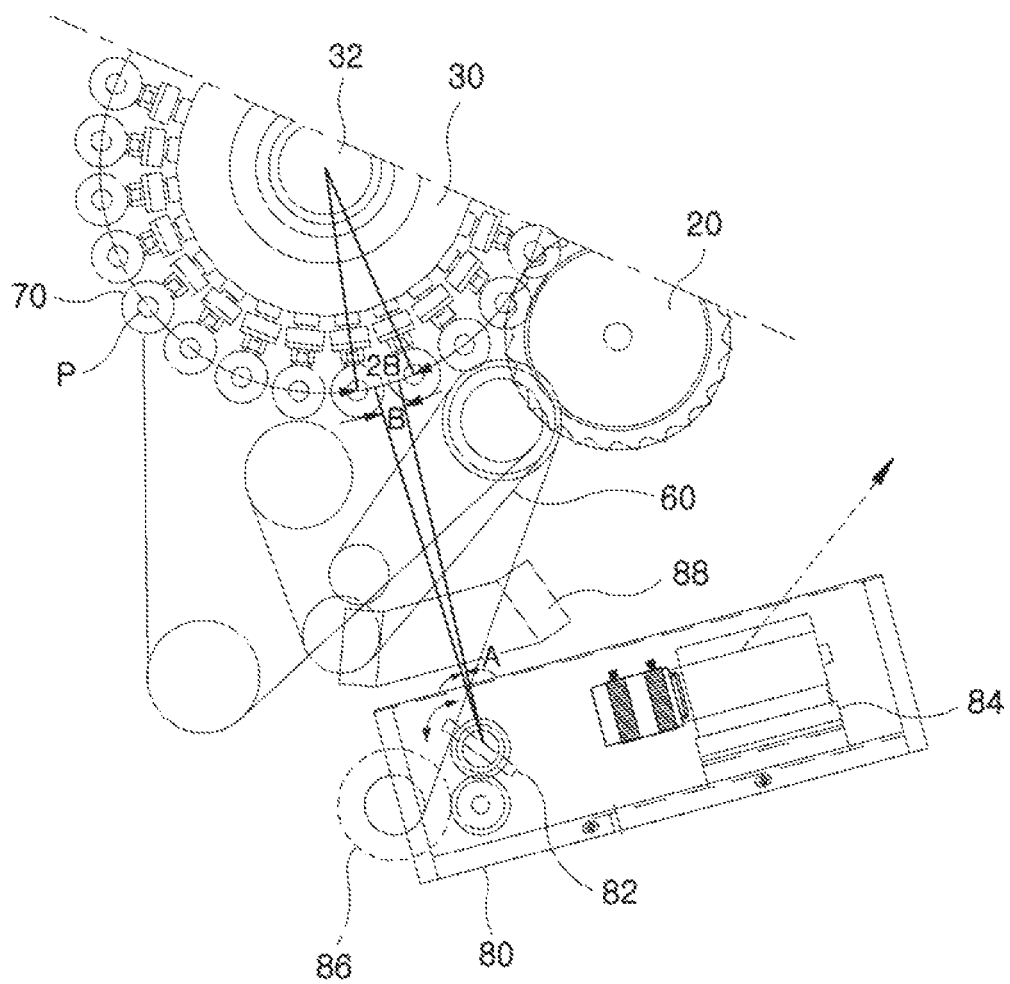
Figure 7A:
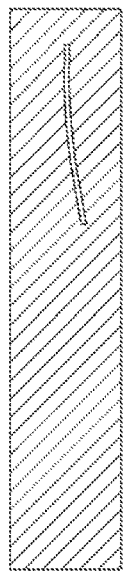
FIGS. 7A to 7F illustrate several shapes of defects discovered from photographed sintered uranium bodies.
Figure 7B:
Figure 7C:
Figure 7D:
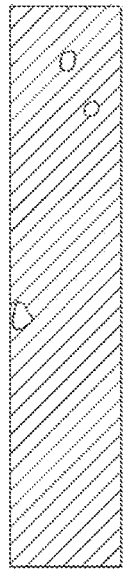
Figure 7E:
Figure 7F:
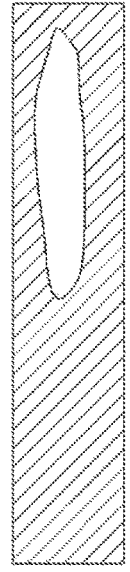

FIGS. 6A and 6B are front views of the photographing unit 80 shown in FIG. 2A in a mechanical cam type and an electric motor (servo) type, respectively.

Referring to FIG. 6A, the photographing unit 80 photographs, in order, the surfaces of the cylindrical bodies p that are moving in the circumferential direction. The photographing unit 80 includes a camera 84 of which position is fixed, a lighting unit 88 which is disposed around the area in which each cylindrical body p is photographed to radiate light toward the cylindrical body p, and a reflector 82 which changes the orientation thereof so that while the cylindrical body p makes one rotation, light reflected by the cylindrical body may travel into the camera 84.

Changing the orientation of the reflector 82 takes place in an interlocked manner with the rotation of the circular conveyor 30. The interval 2B between the clamp units 70 may double a photographing distance B in which the cylindrical body p is photographed. An angle A at which the orientation of the reflector 82 is changed is determined in response to the distance B.

The reflector 82 changes the orientation thereof to the angle A in the corresponding direction while the cylindrical body p makes one rotation (i.e., while it moves in the circumferential direction by the distance B), thus enabling the camera 84 to trace the cylindrical body p and photograph same. Further, the reflector 82 returns to original state thereof while the cylindrical body p makes a subsequent rotation (i.e., while it further moves in the circumferential direction by the distance B). The reflector 82 that has returned to original state thereof repeats the same operation with respect to the subsequent cylindrical body p.

Changing the orientation of the reflector 82 may be realized by a cam 86 that rotates in conjunction with the rotating shaft 32 of the circular conveyor 30. Alternatively, as shown in FIG. 6B, the orientation of the reflector 82 may be changed by an electric motor 89 that is interlocked with a sensor 87 that senses the movement of the circular conveyor 30.

Referring back to FIG. 6A, the camera 84 includes a line-scan camera which photographs the surface of the cylindrical body p in a unit of line, or a frame scan camera which photographs it in a unit of surface. The kind of camera 84 is not limited to a specific type.

In accordance with an embodiment of the present invention, the camera 84 is able to trace the cylindrical body p using the reflector 82 despite being in the fixed position and photograph the surface of the cylindrical body p. Hence, the camera 84 can easily and rapidly photograph the entirety of the surface of the cylindrical body p that corresponds to 360°.

FIGS. 7A to 7F illustrate several shapes of defects discovered from photographed sintered uranium dioxide pellets.

FIGS. 7A to 7F respectively show examples of a circumferential crack, a longitudinal crack, side brokenness, an end-associated defect and an unground portion.

Referring back to FIG. 2A, the control unit 90 analyzes a photographed image of the surface of each cylindrical body p and determines whether the cylindrical body p is defective or not. Furthermore, if there is a cylindrical body p that is determined to be defective, the control unit 90 memorizes the location of the defective cylindrical body p to trace same. Further, the control unit 90 controls the operation of the circular conveyor 30, the clamp unit 70, and the like. In addition, the control unit controls the operation of the lighting unit 88, the camera 84 and the reflector 82 of the photographing unit 80.

Figure 8:
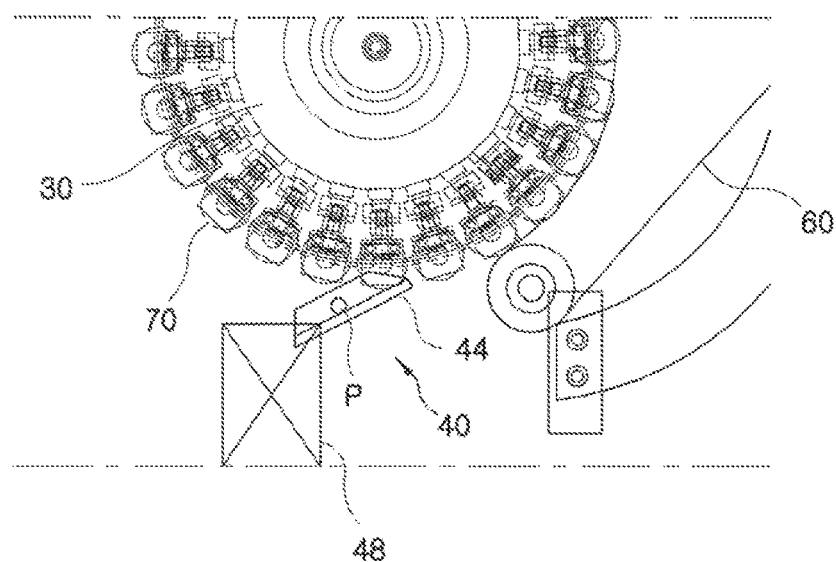
FIG. 8 is a front view of a collection unit shown in FIG. 2A.

FIG. 8 is a front view of the collection unit 40 shown in FIG. 2A.

The collecting unit 40 collects the cylindrical body p that is determined to be defective by the control unit 90. The collecting unit 40 includes a plate 44 and a collection container 48. The plate 44 is positioned in an inclined angle and receives the defective cylindrical body p to guide it into the collection container 48 so that the defective cylindrical bodies p are collected in the collection container 48. The clamp unit 70 releases and puts the cylindrical bodies p that have been clamped on the plate 44. The collection container 48 is attachably and detachably installed and collects the defective cylindrical bodies p from the plate 44.

Figure 9:
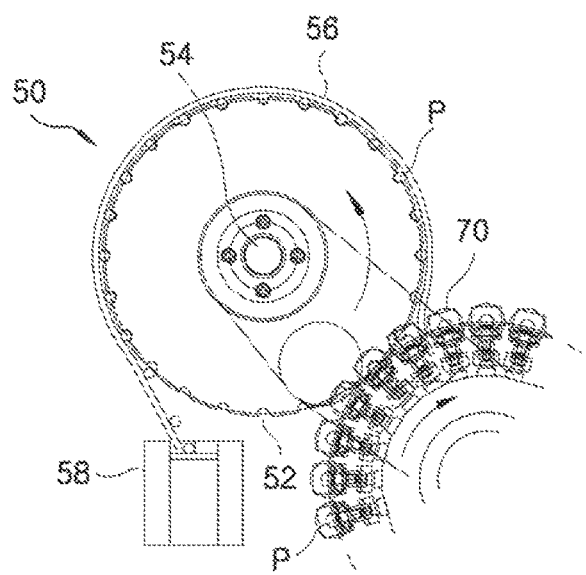
FIG. 9 is a front view of a discharge unit shown in FIG. 2A.

FIG. 9 is a front view of the discharge unit 50 shown in FIG. 2A.

The discharge unit 50 discharges cylindrical bodies p that have been determined to be normal. The construction of the discharge unit 50 is similar to that of the arranging unit 20. In detail, the discharge unit 50 has a shape of a star wheel, which has a plurality of pockets 52 arranged around the circumstance thereof at regular intervals. Accordingly, each cylindrical body p is transferred from the circular conveyor 30 to the discharge unit 50 and inserted into the corresponding pocket 52. When transferring each cylindrical body p from the circular conveyor 30 to the discharge unit 50, the corresponding clamp unit 70 that has clamped the cylindrical body p releases it. The discharge unit 50 and the circular conveyor 30 rotate such that they move in the same direction along the tangent therebetween. The discharge unit 50 includes a guide 56 and a vacuum pump and a transportation unit 58 which transports the cylindrical bodies p to a subsequent process.

In accordance with an embodiment of the present invention, transferring, inspecting and sorting out the cylindrical bodies p can be automatically conducted in a single system. Therefore, labor consumption is minimized, and the efficient utilization of space can be improved.

Hereinafter, the operation of the apparatus for inspecting a surface of the cylindrical body in accordance with the embodiment of the present invention will be described.

In the input unit 10, the toothed wheel 14 rotates and uses teeth thereof, pushing cylindrical bodies p from the tray 12 into the inclined rail 16. The cylindrical bodies p that have been in the standby state in the inclined rail 16 are input one after another into the arranging unit 20 by the force of gravity.

The arranging unit 20 arranges the cylindrical bodies p at regular intervals using the pockets 22. Specifically, as the arranging unit 20 rotates, the cylindrical bodies p that have been in the standby state the inclined rail 16 are inserted one after another into the corresponding pockets 22 and moved in the circumferential direction.

The circular conveyor 30 rotates while keeping in contact with the arranging unit 20. The circular conveyor 30 receives the arranged cylindrical bodies p in order and moves same in the circumferential direction. Here, the rotational speeds of the circular conveyor 30 and the arranging unit 20 are controlled so that the arranged cylindrical bodies p are transmitted to the clamp units 70 at a ratio of 1:1.

Each clamp unit 70 clamps both ends, i.e., the upper and lower surfaces, of the corresponding cylindrical body p. The cylindrical body p may be inserted between and clamped by the two clamp tips 72 of the clamp unit 70. As the circular conveyor 30 rotates, the clamp unit 70 revolves around the circular conveyor 30 and moves the cylindrical bodies p in the circumferential direction. Further, each clamp unit 70 rotates on its own axis, thus rotating the clamped cylindrical body p.

The rotary belt 60 allows each clamp unit 70 to rotate only around the area in which the cylindrical body p is photographed. The rotary belt 60 moves while being interlocked with the rotating shaft 32 of the circular conveyor 30.

The photographing unit 80 photographs, in order, the surfaces of the cylindrical bodies p that are moving in the circumferential direction. The reflector 82 changes the orientation thereof in conjunction with the rotation of the circular conveyor 30. The reflector 82 changes the orientation thereof in the predetermined direction while the corresponding cylindrical body p makes one rotation (i.e., while the cylindrical body p moves in the circumferential direction by the distance B in which it is photographed), thus enabling the camera 84 to trace the cylindrical body p and photograph same. Further, the reflector 82 returns to original state thereof while the cylindrical body p makes a subsequent rotation (i.e., while it further moves in the circumferential direction by the distance B).

The control unit 90 analyzes a photographed image of the surface of each cylindrical body p to determine whether the cylindrical body p is defective or not. The control unit 90 memorizes the location of a cylindrical body p that has been determined to be defective to trace same.

The collecting unit 40 collects cylindrical bodies p that have been determined to be defective by the control unit 90. When it is determined that a cylindrical body p is defective, the corresponding clamp unit 70 that has clamped the defective cylindrical body p releases it onto the plate 44. The plate 44 receives the defective cylindrical body p and guides it into the collection container 48 so that defective cylindrical bodies p can be collected in the collection container 48.

The discharge unit 50 discharges the cylindrical bodies p that have been determined to be normal. The discharge unit 50 receives the normal cylindrical bodies p from the circular conveyor 30 using the pockets 52. The normal cylindrical bodies p are transferred by the transportation unit 58 to a subsequent process.

Through the above-mentioned process, the apparatus for inspecting the surface of cylindrical body in accordance with the embodiment of the present invention can rapidly and precisely inspect whether the surfaces, especially, the side surfaces, of cylindrical bodies, such as sintered uranium dioxide pellets and the like, are defective or not.

While the invention has been shown and described with respect to the embodiments, the present invention is not limited thereto. It will be understood by those skilled in the art that various changes and modifications may be made without departing from the scope of the invention as defined in the following claims.

What is claimed is:

1. An apparatus for inspecting an outside surface of cylindrical bodies, comprising:
    an arranging unit having a circumference, a plurality of pockets disposed at regular intervals around the circumference, each of the cylindrical bodies inserted into each of the pockets;
    a circular conveyor configured to rotate while keeping in contact with the arranging unit, receive the cylindrical bodies in order and move the received cylindrical bodies in a circumferential direction, wherein the circular conveyor includes a rotating shaft;
    a plurality of clamp units arranged around a circumference of the circular conveyor at predetermined intervals and configured to receive and clamp the cylindrical bodies in order, the clamp units being configured to rotate on the clamp units' own axes so as to rotate the clamped cylindrical bodies;
    a photographing unit configured to photograph entire outside surfaces of the clamped cylindrical bodies in order;
    a control unit configured to analyze the outside surface of each of the cylindrical bodies and determine whether the outside surface is defective or not;
    a rotary belt configured to rotate while keeping in contact with the clamp units and to allow the clamp units to rotate on the clamp units' own axes only in an area in which each of the clamped cylindrical bodies is photographed; and
    a belt drive shaft configured to move the rotary belt,
    wherein the control unit is configured to control an interlocking operation of the circular conveyor and the clamp units such that said each of the cylindrical bodies is clamped and rotated by one rotation by while the clamp units are moved by the circular conveyor in the circumferential direction thereof by a specific distance, and
    the control unit is further configured to control an interlocking operation of the clamp units and the photographing unit such that while said each of the cylindrical bodies makes the one rotation, the photographing unit traces said each of the cylindrical bodies to photograph same, thereby to photograph an entire side surface of the outside surface of said each of the cylindrical bodies that corresponds to 360°,
    wherein said each of the clamp units is configured to be rotated by the rotary belt being interlocked with a rotating shaft of the circular conveyor,
    wherein the photographing unit comprises:
    a camera;
    a lighting unit configured to radiate light onto said each of the cylindrical bodies; and
    a reflector configured to change an orientation of the reflector so that light reflected by the cylindrical body travels into the camera while the cylindrical body makes one rotation,
    wherein the orientation of the reflector is changed by a cam that rotates in conjunction with the rotating shaft of the circular conveyor, and
    wherein the belt drive shaft is rotated in conjunction with the rotating shaft of the circular conveyor.

2. The apparatus of claim 1, wherein the reflector is configured to change the orientation thereof in conjunction with rotation of the circular conveyor so that the reflector changes the orientation thereof in a specific direction while said each of the cylindrical bodies makes one rotation, and
    wherein the reflector is configured to return to the original state thereof while said each of the cylindrical bodies makes a subsequent rotation.

3. The apparatus of claim 2, wherein each of the predetermined intervals between the clamp units is double that of the specific distance.

4. The apparatus of claim 1, wherein said each of the clamp units includes two clamp tips disposed spaced apart from each other, said each of the clamp units configured to clamp said each of the cylindrical bodies by pressing an upper surface and a lower surface thereof with the clamp tips, respectively, and
  wherein each of the clamp tips is made of either a soft material or a hard material.

5. The apparatus of claim 1, wherein the arranging unit has a shape of a star wheel, which rotates in the circumferential direction.

6. The apparatus of claim 5, wherein rotational speeds of the circular conveyor and the arranging unit are controlled such that the cylindrical bodies are transmitted to the clamp units one by one.

7. The apparatus of claim 5, wherein the arranging unit comprises:
  a guide configured to be formed outside the pockets in the circumferential direction of the arranging unit to prevent the cylindrical bodies inserted into the pockets from being removed therefrom.

8. The apparatus of claim 1, further comprising:
  an input unit including a inclined rail, a tray and a toothed wheel,
  wherein the cylindrical bodies are loaded in the tray; and
  the toothed wheel is configured to rotate and push the cylindrical bodies one after another from the tray into the inclined rail, and
  wherein the input unit is configured to input the cylindrical bodies that have been in a standby state in the inclined rail into the arranging unit.

9. The apparatus of claim 1, further comprising a collecting unit configured to collect the cylindrical bodies which are determined to be defective by the control unit,
  wherein the collecting unit comprises:
    a plate configured to be inclined at a specific angle, receive the defective cylindrical bodies from the clamp unit and guide the defective cylindrical bodies downwards; and
    a collection container configured to be attachably and detachably provided and collect the defective cylindrical bodies from the plate.

10. The apparatus of claim 9, further comprising a discharge unit configured to discharge the cylindrical bodies which are determined to be normal by the control unit,
  the discharge unit configured to receive the normal cylindrical bodies from the circular conveyor and have a shape of a star wheel, which has a plurality of pockets arranged around a circumference thereof at regular intervals so that the normal cylindrical bodies are inserted into the pockets.

11. The apparatus of claim 1, wherein said each of the cylindrical bodies comprises a sintered uranium dioxide pellet used as a nuclear fuel for a light-water reactor.

12. The apparatus of claim 1, further comprising a vacuum pump configured to adsorb the outside surface of said each of the cylindrical bodies inserted into each of corresponding pockets.

13. A method for inspecting an outside surface of cylindrical bodies, comprising:
  providing the cylindrical bodies to an arranging unit having a circumference, wherein a plurality of pockets are disposed at regular intervals around the circumference and each of the cylindrical bodies inserted into each of the pockets;
  arranging the cylindrical bodies by the arranging unit;
  providing the arranged cylindrical bodies from the arranging unit to a circular conveyor, wherein the circular conveyor is configured to rotate while keeping in contact with the arranging unit, receive the cylindrical bodies in order and move the received cylindrical bodies in a circumferential direction, wherein the circular conveyor includes a rotating shaft;
  clamping each of the provided cylindrical bodies by clamp units arranged around a circumference of the circular conveyor at predetermined intervals, wherein the clamp units is configured to rotate on the clamp units' own axes so as to rotate the clamped cylindrical bodies; and
  photographing entire outside surface of each of the clamped cylindrical bodies in order by a photographing unit,
  wherein during the photographing, the control unit controls an interlocking operation of the circular conveyor and the clamp units such that each of the cylindrical bodies is clamped and rotated by one rotation by the corresponding clamp unit while it is moved by the circular conveyor in the circumferential direction thereof by a specific distance,
  wherein the clamp units rotate on the clamp units' own axes only in an area in which each of the clamped cylindrical bodies is photographed,
  wherein the clamp units are configured to rotate while keeping in contact with a rotary belt,
  wherein the rotary belt is configured to be moved by a belt drive shaft,
  wherein the photographing unit comprises:
  a camera;
  an lighting unit configured to radiate light onto said each of the cylindrical bodies; and
  a reflector configured to change an orientation of the reflector so that light reflected by the cylindrical body travels into the camera while the cylindrical body makes one rotation,
  wherein the orientation of the reflector is changed by a cam that rotates in conjunction with the rotating shaft of the circular conveyor, and
  wherein the belt drive shaft is rotated in conjunction with the rotating shaft of the circular conveyor.

14. The method of claim 13,
  wherein during the photographing, the reflector is controlled to change the orientation thereof to a predetermined angle corresponding to the specific distance while each of the cylindrical bodies is rotated by one rotation.

15. The method of claim 14, wherein the reflector changes the orientation thereof in conjunction with rotation of the circular conveyor so that the reflector changes the orientation thereof in a specific direction while said each of the cylindrical bodies makes one rotation, and the reflector returns to the original state thereof while said each of the cylindrical bodies makes a subsequent rotation.

16. The method of claim 15, wherein each of the predetermined intervals between the clamp units is double that of the specific distance.

* * * * *